United States Patent
De Haan et al.

(10) Patent No.: US 12,134,592 B2
(45) Date of Patent: Nov. 5, 2024

(54) SEPARATION METHOD AND REACTOR SYSTEM FOR A GLYCOL-WATER MIXTURE

(71) Applicant: Ioniqa Technologies B.V., Eindhoven (NL)

(72) Inventors: Andre Banier De Haan, Eindhoven (NL); Jan Volkert Zander, Eindhoven (NL)

(73) Assignee: Ioniqa Techonolgies B.V. (NL)

( * ) Notice: Subject to any disclaimer, the term of this patent is extended or adjusted under 35 U.S.C. 154(b) by 406 days.

(21) Appl. No.: 17/294,633

(22) PCT Filed: Nov. 20, 2019

(86) PCT No.: PCT/EP2019/081981
§ 371 (c)(1),
(2) Date: May 17, 2021

(87) PCT Pub. No.: WO2020/104552
PCT Pub. Date: May 28, 2020

(65) Prior Publication Data
US 2022/0009864 A1 Jan. 13, 2022

(30) Foreign Application Priority Data
Nov. 21, 2018 (NL) .................................. 2022037

(51) Int. Cl.
*C07C 29/80* (2006.01)
*B01D 3/00* (2006.01)
(Continued)

(52) U.S. Cl.
CPC ............. *C07C 29/80* (2013.01); *B01D 3/007* (2013.01); *B01D 3/06* (2013.01); *B01D 3/146* (2013.01);
(Continued)

(58) Field of Classification Search
CPC .. B01D 3/146; B01D 3/148; C07C 29/80–84; C07C 31/202
See application file for complete search history.

(56) References Cited

U.S. PATENT DOCUMENTS 2,218,234 A 10/1940 Fisher
2,510,548 A * 6/1950 Brunjes .................. B01D 3/146
159/31
(Continued)

FOREIGN PATENT DOCUMENTS

CN 205832659 U 12/2016
JP S473506 B 2/1972
(Continued)

OTHER PUBLICATIONS

PE2E translation of KR-20190125641-A.*
(Continued)

*Primary Examiner* — Jonathan Luke Pilcher
(74) *Attorney, Agent, or Firm* — Husch Blackwell LLP

(57) ABSTRACT

The separation method separates a polyalcohol compound from water, so as to obtain a purified product stream comprising the polyalcohol compound in output concentration of at least 90 wt %. Thereto, a mixture of the polyalcohol compound and water is provided, said mixture having a polyalcohol concentration. The polyalcohol concentration of mixture is increased in an evaporation stage, at least a portion of which is operated in at first pressure. Subsequently, the mixture is treated in distillation stage to be deliver the stream comprising the polyalcohol compound in the output concentration of at least 90 wt %, which distillation stage is operated at a second pressure. Herein, the distillation stage is operated to produce steam output, that optionally compressed to a third pressure and is coupled to the evaporation stage. The second pressure and/or any third (Continued)

Figure 1:
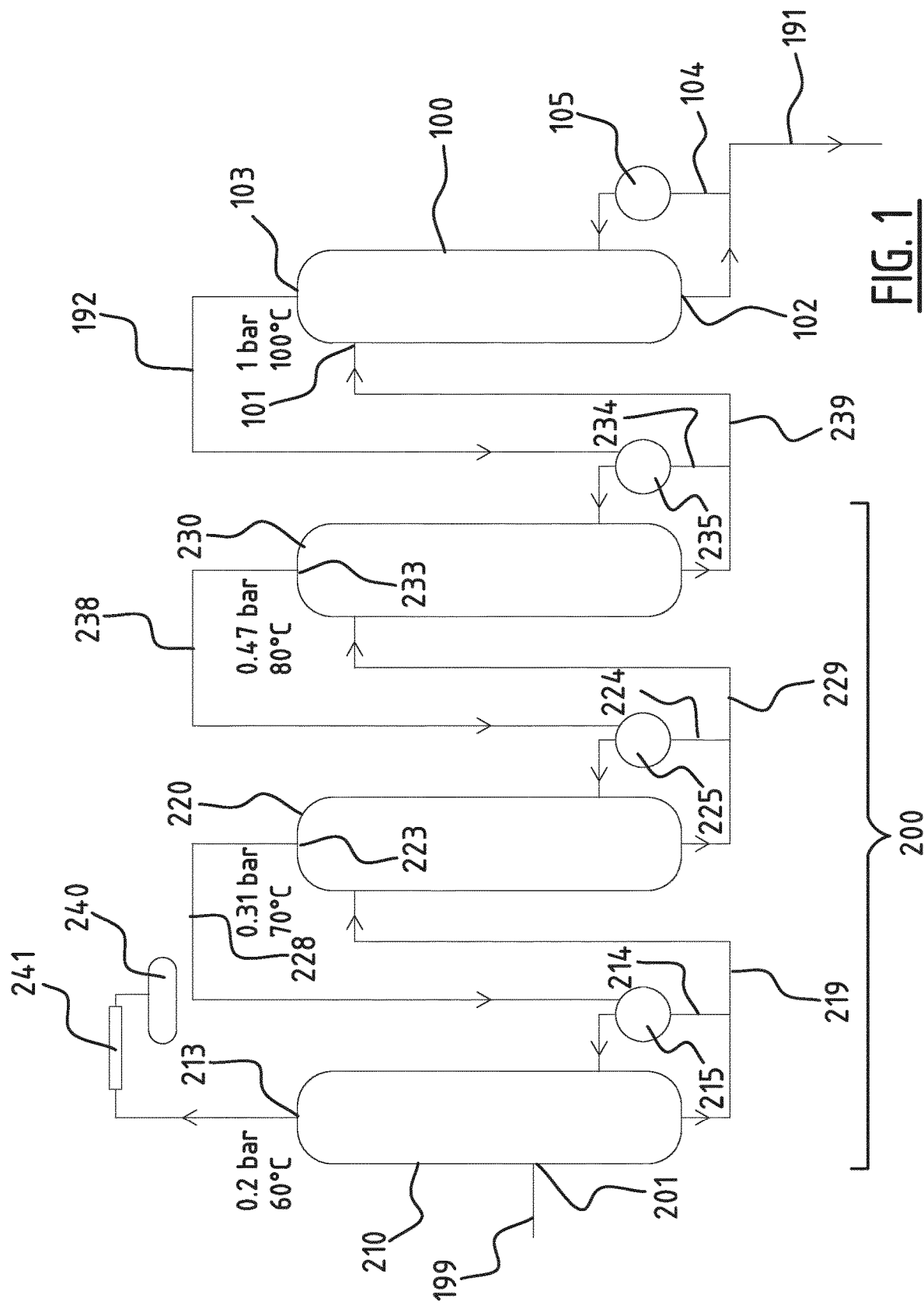

pressure is higher than first pressure. The reactor system is configured for performing the separation method.

13 Claims, 11 Drawing Sheets

(51) Int. Cl.
    *B01D 3/06*           (2006.01)
    *B01D 3/14*           (2006.01)
    *B01D 3/32*           (2006.01)
    *C08J 11/24*         (2006.01)

(52) U.S. Cl.
    CPC ............. *B01D 3/148* (2013.01); *B01D 3/322* (2013.01); *C08J 11/24* (2013.01); *C08J 2367/02* (2013.01)

(56) References Cited

U.S. PATENT DOCUMENTS

| | | | |
|---|---|---|---|
| 3,367,847 A * | 2/1968 | Pierson | C08G 63/16 |
| | | | 203/84 |
| 3,875,019 A * | 4/1975 | Cocuzza | B01D 53/263 |
| | | | 203/18 |
| 3,878,055 A | 4/1975 | Cox et al. | |
| 4,225,394 A * | 9/1980 | Cox | B01D 3/148 |
| | | | 203/18 |
| 4,332,643 A | 6/1982 | Reid | |
| 5,209,825 A * | 5/1993 | Badat | C07C 29/80 |
| | | | 549/429 |
| 5,234,552 A | 8/1993 | McGrew et al. | |
| 5,269,933 A | 12/1993 | Jehle et al. | |
| 6,080,897 A * | 6/2000 | Kawabe | C07C 29/12 |
| | | | 549/230 |
| 6,444,095 B1 * | 9/2002 | Evans | C07C 41/42 |
| | | | 202/160 |
| 9,943,775 B2 * | 4/2018 | Esquier | B01D 53/1425 |
| 2005/0072663 A1 | 4/2005 | Laborie et al. | |
| 2008/0154071 A1 * | 6/2008 | Husen | C07C 45/80 |
| | | | 568/862 |
| 2018/0118659 A1 | 5/2018 | Hiles et al. | |
| 2018/0290073 A1 | 10/2018 | Brown et al. | |
| 2023/0234904 A1 * | 7/2023 | Wolters | C07C 29/80 |
| | | | 568/868 |

FOREIGN PATENT DOCUMENTS

| | | | | |
|---|---|---|---|---|
| JP | S4844633 A | | 12/1973 | |
| KR | 20190125638 A | * | 11/2019 | ............ B01D 3/06 |
| KR | 20190125641 A | * | 11/2019 | ............ B01D 3/06 |
| KR | 20190127054 A | * | 11/2019 | ............ B01D 3/06 |
| WO | 2008070608 A1 | | 6/2008 | |

OTHER PUBLICATIONS

PE2E translation of KR-20190125638-A.*
PE2E translation of KR-20190127054-A.*
International Search Report re application No. PCT/EP2019/081981, dated Mar. 3, 2020.
Written Opinion re application No. PCT/EP2019/081981, dated Mar. 3, 2020.

* cited by examiner

SEPARATION METHOD AND REACTOR SYSTEM FOR A GLYCOL-WATER MIXTURE

This application is a 371 of international application PCT/EP2019/081981 filed on Nov. 20, 2019 which is incorporated herein by reference.

FIELD OF THE INVENTION

The invention relates to a method of at least partially separating a polyalcohol compound from water, so as to obtain a purified product stream comprising the polyalcohol compound in an output concentration of at least 90 wt %, which method comprises the steps of providing a mixture of the polyalcohol compound and water, and treating the mixture in a distillation stage to increase a concentration of the polyalcohol compound.

The invention further relates to a reactor system to carry out the method.

BACKGROUND OF THE INVENTION

Polyalcohol compounds such as glycols are used in a variety of chemical processes including natural gas purification, preparation of ethylene oxide, polyethylene glycol and polypropylene glycol as well as the polymerisation of polyesters, such as polyethylene terephthalate (PET) and the depolymerisation of such polyesters, typically as one step of recycling of waste material. One of the glycols that is most commonly used, is ethylene glycol.

Typically, as a result of the use of these glycols, a mixture with water is obtained. A well-known issue in the art is that the regeneration of a pure or almost pure stream of the glycol or other polyalcohol compound requires vacuum distillation and other treatments that cost a lot of energy. Moreover, there is a risk that additional compounds present in the mixture, would be evaporated as well, potentially leading to environmental contamination. As a consequence, several processes have been envisaged for the purification of glycols from water, including reverse osmosis, membrane distillation, pervaporation, vacuum distillation, ozonisation, use of activated carbon absorption, aldehyde separation through stripping and ion exchange. Many of these methods focus on the reduction of the concentration of glycol in an aqueous waste stream. For purification of a mixture to obtain purified glycol or other polyalcohols, typical approaches are (vacuum) distillation, reverse osmosis, pervaporation, and/or combinations thereof.

One specific method is known from U.S. Pat. No. 2,218,234. This patent discloses a method for the separation of isopropyl alcohol (50-75%), ethylene glycol (10-30%), water, dyes and salts (5-15% in total). In a first step, the mixture is treated by distillation, so as to remove the isopropyl alcohol and some water. The residue passes to a feed tank and is from there supplied to another distillation column. A hydrocarbon boiling below 140° C., such as toluene, is then added into the second distillation column as a vapor. Due to the presence of the toluene, there is no particular dehydration of the glycol, but the toluene carries over the glycol and water at temperatures around 109° C. Hence, it does not provide an effective method for the removal of the water from the glycol.

Another method is known from U.S. Pat. No. 4,332,643. This method has the object to provide a glycol such as triethylene glycol, in a concentration of at least 99.9%, starting from a "dilute" mixture of water and a glycol. This dilute mixture is used as the reflux condenser coolant, where it is heated to 140-150° F. (60-65° C.) led to a three-phase separator, wherein any gas is separated off. It has then a concentration of about 94.5% by weight and is led to a distillation column, in which it is concentrated to 98.5-99.0 wt. %. The concentrated glycol goes to a reboiler operating at a temperature of 198° C., and then to a water exhauster operating at a temperature of 198-221° C. This is an expensive process to achieve water-free glycol, while the initial concentration is already above 90 wt %.

Again a further method and system is known from U.S. Pat. No. 5,234,552. Object of the disclosed invention is to prevent the emission of aromatic compounds into the atmosphere during glycol dehydration. Such emissions include water and hydrocarbons as liquids in vapor form. The disclosed system includes a low temperature separation system to separate usable gas and hydrocarbons coming from a distillate well. Therein, a desiccant such as diethylene glycol, triethylene glycol is injected, which leaves the separator as a mixed stream of glycol and water with some hydrocarbons. This stream is transferred to a glycol reboiler operating at a temperature of 350-400° F. (177-204° C.). However, this temperature is far above the atmospheric boiling point of water. In other words, it is not an energy-efficient method, and one would like to improve this.

An alternative method is known from U.S. Pat. No. 5,269,933. Herein a glycol/water mixture with a glycol concentration of about 20 wt % (generally 5-70 wt %) is enriched in glycol to a concentration of at least 90%, preferably at least 95 wt %. The glycol/water mixture is thereto first treated by distillation, which may be carried out at a normal pressure as well as at a reduced pressure (vacuum distillation). The next step is the concentration of the organic fluid by the application of a pervaporation with the use of water-selective membranes and a pressure at the permeate side of 20-150 mbar. The water stream obtained from the distillation is further treated with reverse osmosis with a pressure of 20-70 bar. However, the low pressure of the pervaporation (below 0.2 bar) is deep vacuum and the pressure of the reverse osmosis is high. Both complicate operation.

SUMMARY OF THE INVENTION

Therefore, there is still a need for an energy-efficient process for the dehydration of a polyalcohol compound, such as a glycol, in which the use of very high and very low pressures is prevented or at least significantly limited.

There is also a need for a reactor system in which such process can be implemented.

Accordingly, according to a first aspect, the invention provides a method of at least partially separating a polyalcohol compound from water, so as to obtain a purified product stream comprising the polyalcohol compound in an output concentration of at least 90 wt %. The method of the invention comprises the steps of (1) providing a mixture of the polyalcohol compound and water, said mixture having a polyalcohol concentration: (2) increasing the polyalcohol concentration of the mixture in an evaporation stage, at least a portion of which is operated at a first pressure: (3) treating the mixture in a distillation stage to be delivered the stream comprising the polyalcohol compound in the output concentration of at least 90 wt %, which distillation stage is operated at a second pressure. According to the invention, the distillation stage is operated to produce steam output, that is optionally compressed to a third pressure and is coupled to the evaporation stage by means of heat exchanging, wherein second pressure and/or any third pressure is higher than the first pressure.

According to a second aspect, the invention provides a reactor system for the separation of a polyalcohol compound from water, so as to obtain a purified product stream comprising the polyalcohol compound in an output concentration of at least 90 wt %. The reactor system of the invention comprises an evaporation stage comprising an inlet for a mixture of the polyalcohol compound in water and an outlet for a stream enriched in the polyalcohol compound, said evaporation stage being configured for operation, at least in part of said evaporation stage, at a first pressure. The reactor system further comprises a distillation stage comprising an inlet for the stream enriched in the polyalcohol compound arriving from the evaporation stage, an outlet for the purified product stream, and an outlet for a steam output, said distillation stage being configured for operation at a second pressure, wherein the steam output is coupled to the evaporation stage by means of heat-exchanging, and wherein the steam output is optionally compressed to a third pressure, such that the second pressure or any third pressure is higher than the first pressure.

It has been found by the inventors that the boiling point of the water-glycol mixture tends to increase rapidly with the concentration of ethylene glycol, particularly when the glycol concentration is above 50 wt % rather than around 20 wt %, such as in U.S. Pat. No. 5,269,933. However, such an increase can be prevented, or at least strongly inhibited, by arranging the evaporation and distillation stages in a series wherein the pressure is increased from the first to the last stage rather than the opposite, as is typical in installations with multiple distillation stages or effects. In addition, the energy efficiency is maintained in that the steam from the distillation stage is used for heating at least one part of the evaporation stage. Thereto, the steam output is coupled to a column or effect in the evaporation stage. When the evaporation stage comprises a distillation column and/or flash vessel, the coupling occurs via a heat-exchanger. Suitably, the heat exchanger exchanges heat between a stream of steam and part of an outlet stream of the mixture, said part being returned into the said distillation column or flash vessel. When the evaporation stage comprises an installation for multi-effect distillation, the stream of steam may be applied to heating channels thereof. Preferably, the system is configured such that an evaporation temperature within the stage, as defined at atmospheric pressure, is at most 30° C., more preferably at most 20° C. above the boiling point of pure water at atmospheric pressure.

In one suitable embodiment of the invention, the evaporation stage comprises at least one flash vessel. Such a flash vessel is a well-known, robust apparatus in the process industry. It has the advantage that it may absorb additional energy that is supplied temporarily, such as from time to time, when heat becomes available, such as when emptying another reactor operated at a high temperature. In order to transfer such energy that becomes available intermittently, one may use a buffer tank. Alternatively, one may add material from said other reactor directly into the distillation stage. The added heat is then transferred to the evaporation stage via the heat-exchanger. It is preferable to use a plurality of flash vessels in series. Such a series of reactors (or vessels) enables that the pressure can be increased in steps and that each of the reactors may be configured so that the amount of evaporated water is similar or equal in each of them. The term 'similar' refers herein to a variation of at most 25%.

Preferably, the at least one flash vessel is provided with a reboiler. This is an effective means to generate steam at the bottom side of the flash vessel. The reboiler may be external or internal to the flash vessel, as known to the skilled person. Preferably, heat required for operation of the reboiler is supplied from a vessel located more downstream. Particularly a vapour stream leaving such downstream vessel is deemed appropriate thereto. It is observed that in accordance with the invention, a more downstream vessel is operated at a higher pressure. Therefore, the temperature of the vapour from such downstream vessel is higher than the temperature of the vessel to which the reboiler is coupled. Hence, the heat exchange will be very effective.

In a further embodiment, the at least one flash vessel comprises distillation trays between a feed inlet and an inlet from a recycle stream from the reboiler. In an embodiment wherein the evaporation stage comprises a plurality of vessels, such as a first, second and third vessel in series, it is highly preferred that that the third and second vessel are provided with such distillation trays. It has been found that the presence of such distillation trays allows to reduce energy consumption significantly. Preferably the number of distillation trays per vessel is at least two, for instance up to 10, more preferably in the range up to 6, such as 3-5. Still, the vessel is not a distillation column, as it does not contain any means for refluxing. As a consequence, whereas the temperature in a distillation column runs between the boiling point of the first component (i.e. the polyalcohol) and the second component (i.e. water), this is not necessary in the flash vessel with distillation trays. It goes without saying that the number of distillation trays does not need to be the same for all the available vessels.

Alternatively, the evaporation stage is embodied at least partially as a multi-effect distillation installation. The use hereof is cost-effective. Furthermore, if so desired or needed, the pressures may be set within the multi-effect distillation installation with a low minimum pressure without need of specific constructions or safety measures. In other words, the minimum pressure in a multi-effect distillation can be lower than that when using flash vessels and columns without the need for big volumes or additional safety means. The ability of using lower minimum pressures, for instance down to 0.2 bar has the advantage that the distillation stage may be operated at atmospheric pressure and that no compression on the steam output of the distillation stage is required. The number of effects in such multi-effect distillation installation is preferably at least 3. It is observed for clarity that the multi-effect distillation may of course be combined with the presence of one flash vessel or even more vessels. However, it seems more advantageous to choose either for multi-effect distillation or flash vessels as the technological implementation of the evaporation stage.

In a further embodiment, a concentration stage is provided downstream of the evaporation stage and upstream of the evaporation stage. Whereas the heat in the evaporation stage is preferably provided, ultimately, from the distillation stage, the heat supplied to the concentration stage originates from a source external to the reactor system for the separation of the polyalcohol compound from water. For instance, the heat may be waste heat from a reactor, for instance the reactor from which the feed is supplied into the evaporation stage. The heat is supplied to the mixture in the concentration stage by means of heat exchange. Such could be a conventional heat exchanger, or an evaporation apparatus provided with a circulation system for the waste heat (in the form of a vapour or a liquid). A most preferred implementation of such concentration stage is as an evaporator designed in as a multi-effect installation, and more preferably structurally similar to a multi-effect distillation installation used for the evaporation stage.

As mentioned before, it is an option according to the invention, that the steam output of the distillation stage is compressed in a steam compressor. The use of a steam compressor allows that the distillation stage is operated at atmospheric pressure or close to atmospheric pressure, for instance up to 1.5 atmosphere. This has a major advantage if the mixture of the polyalcohol compound and water comprises any additives. The use of a higher pressure implies that the temperature of the stage also increases. At such conditions, a risk occurs that any additives undergo a reaction, for instance with the polyalcohol or with any oxygen in the air, or with other additives present. More particularly, in case that oligomers obtained in the depolymerisation of polyesters are present in the said mixture, these oligomers may colorize the mixture. Such colorization is highly undesired, as the purified product stream would not be acceptable any longer as such.

Typically, when using a plurality of vessels, preferably flash vessels comprising distillation trays at tan area between feed inlet and steam inlet, the compressed steam would be led to the vessel arranged at a most downstream position in the evaporation stage, in other words the vessel directly preceding the distillation stage. The advantage hereof is that such most downstream vessel may be operated at or around atmospheric pressure.

Alternatively or additionally, it is feasible to apply steam compression on a steam output from a first vessel or effect in the evaporation stage. The compressed steam output is led to a steam output of a further vessel or effect. Herein, the first vessel or effect operates at a reduced pressure relative to the further vessel or effect. In this embodiment, the steam compression is not applied on a stream of steam that goes back from the distillation stage to the evaporation stage, so as to maintain a pressure difference. Rather, the steam compression is applied on a steam output from a low pressure vessel or effect to ensure that such steam is upgraded to the higher pressure of the further vessel or effect.

In case that a concentration stage is present between the evaporation stage and the distillation stage, the steam output from the distillation stage is reused in the evaporation stage, thus passing over any vessel or effect in the concentration stage.

While the reactor system and method are feasible for any type of polyalcohol compounds, glycol compounds are deemed advantageous. A preferred glycol compound is ethylene glycol. Suitably, the initial concentration of the mixture of polyalcohol compound and water is at least 40 wt % polyalcohol compound. Preferably, the initial concentration is even higher, such as at least 45 wt % or even at least 50 wt %. More preferably, the method is used for the regeneration of ethylene glycol as used in the depolymerisation of a polyester, such as polyethylene terephthalate.

BRIEF INTRODUCTION OF THE FIGURES

Figure 2:
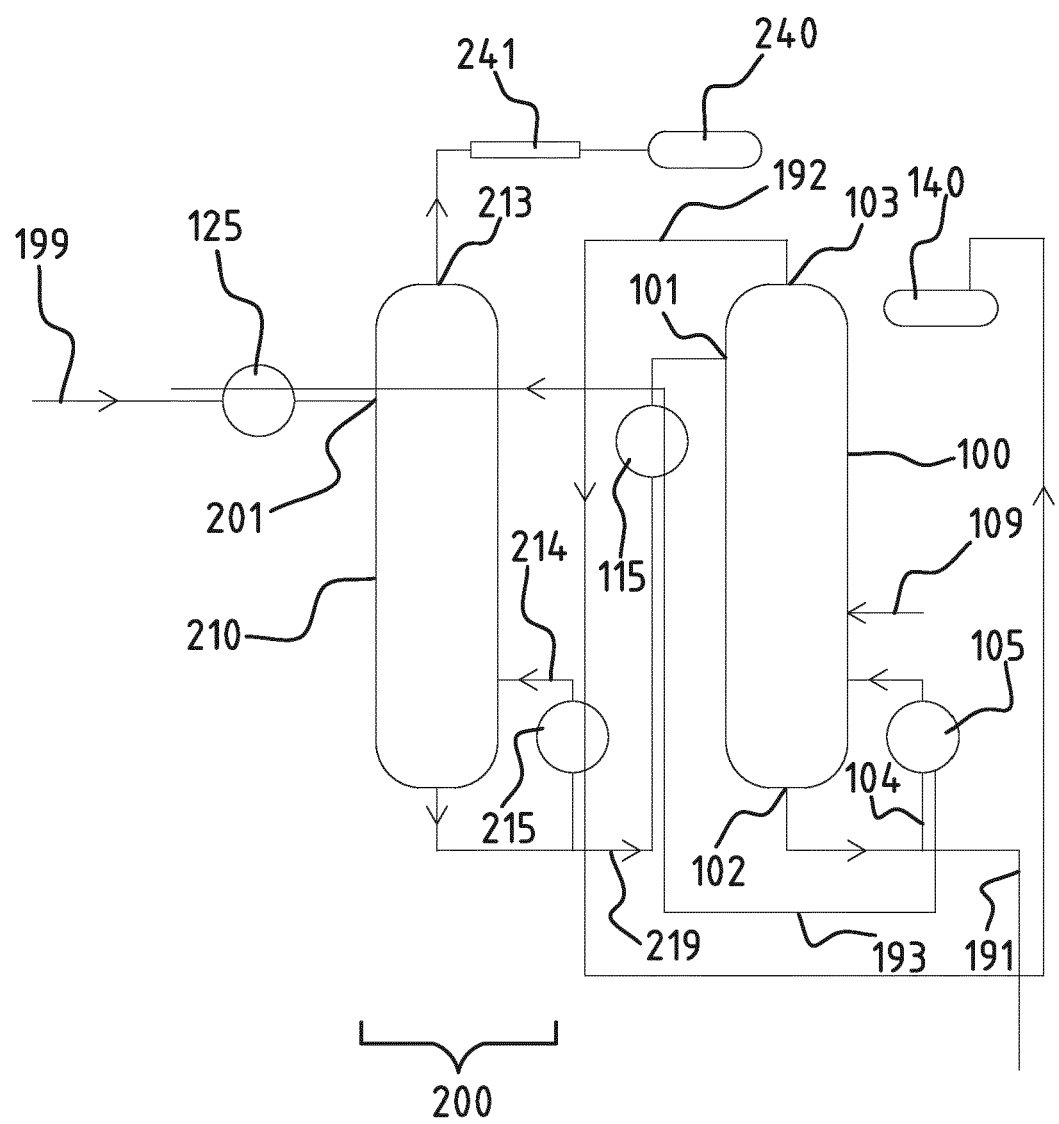
Figure 3:
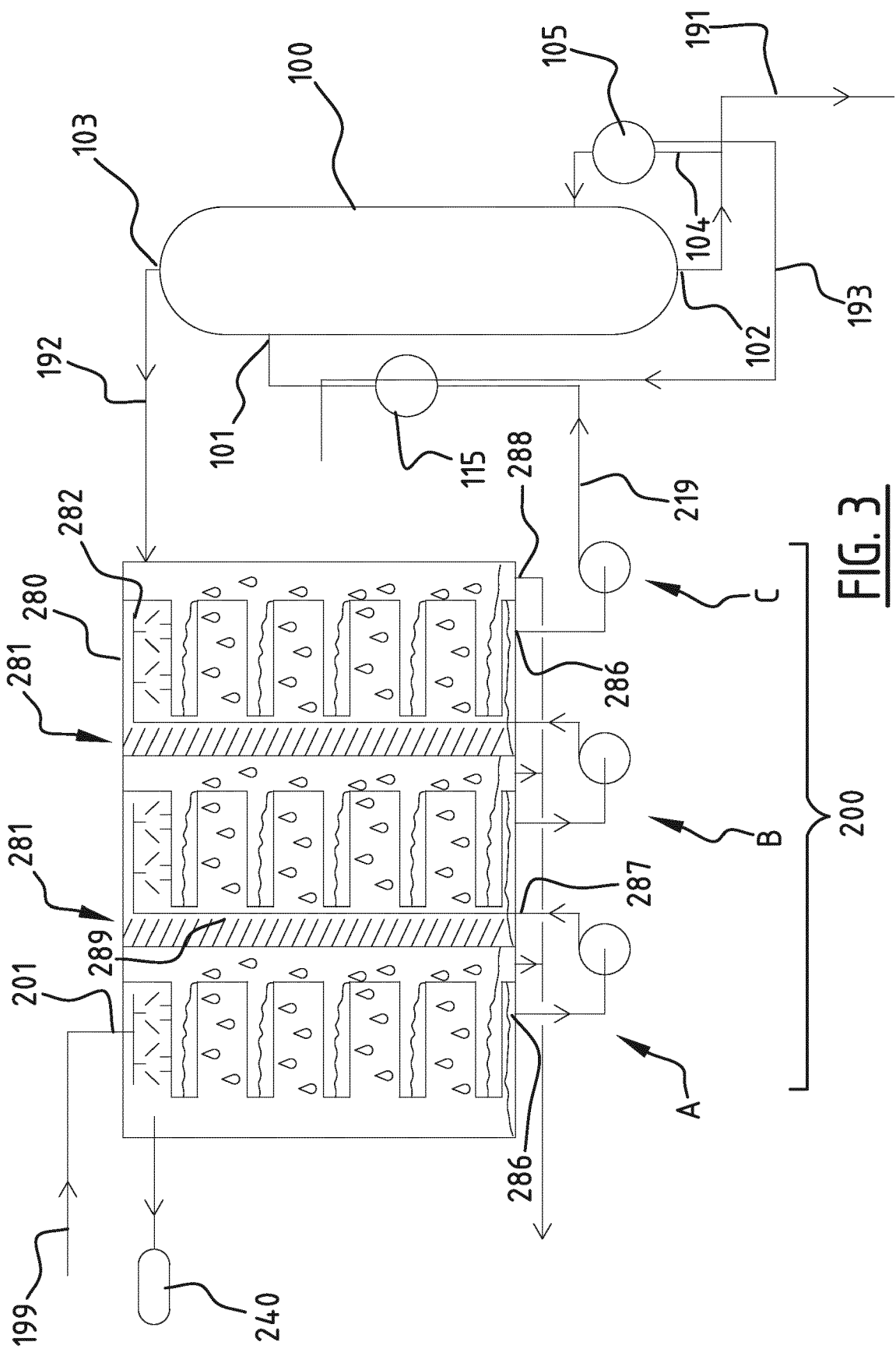
Figure 4:
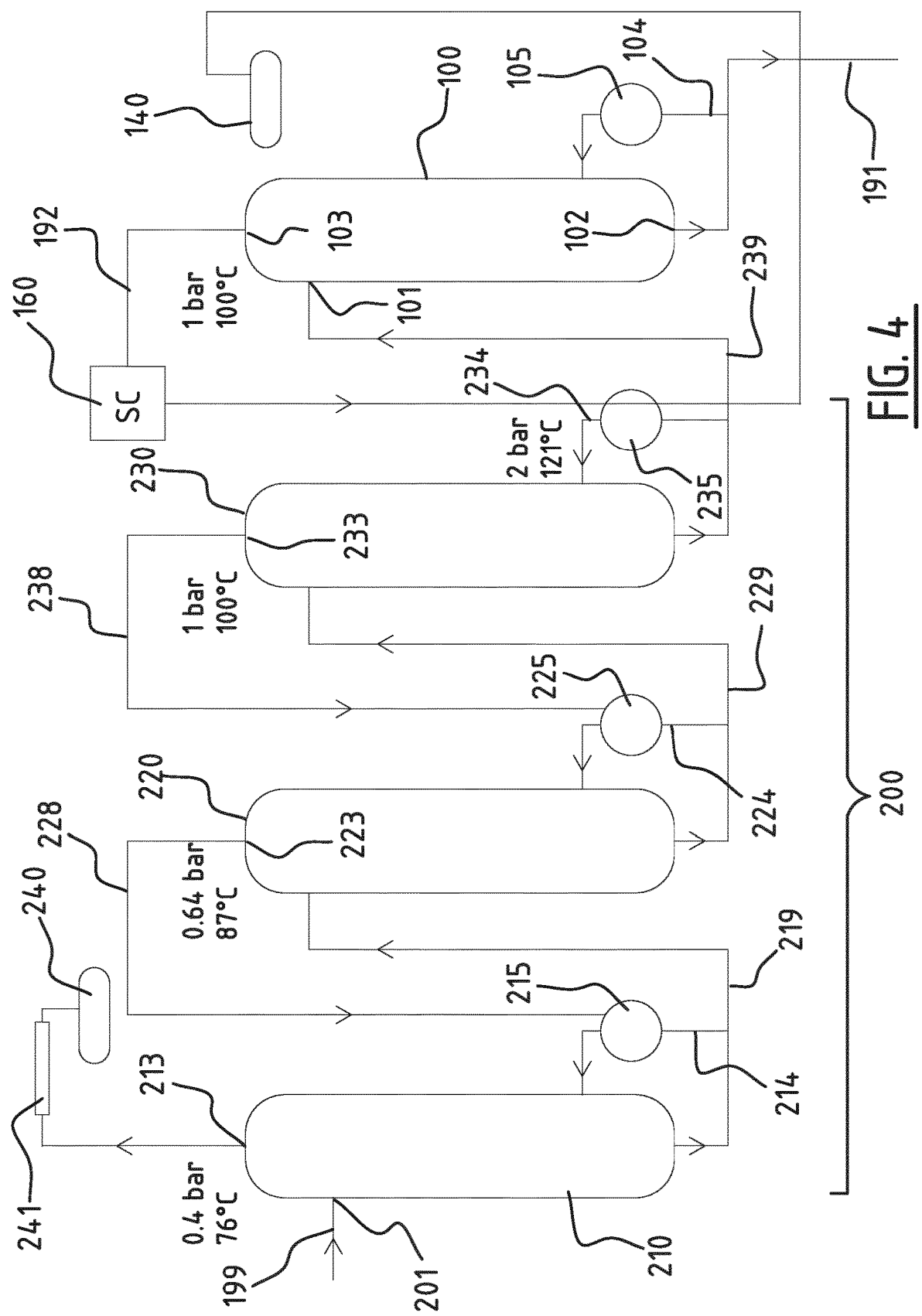
Figure 5:
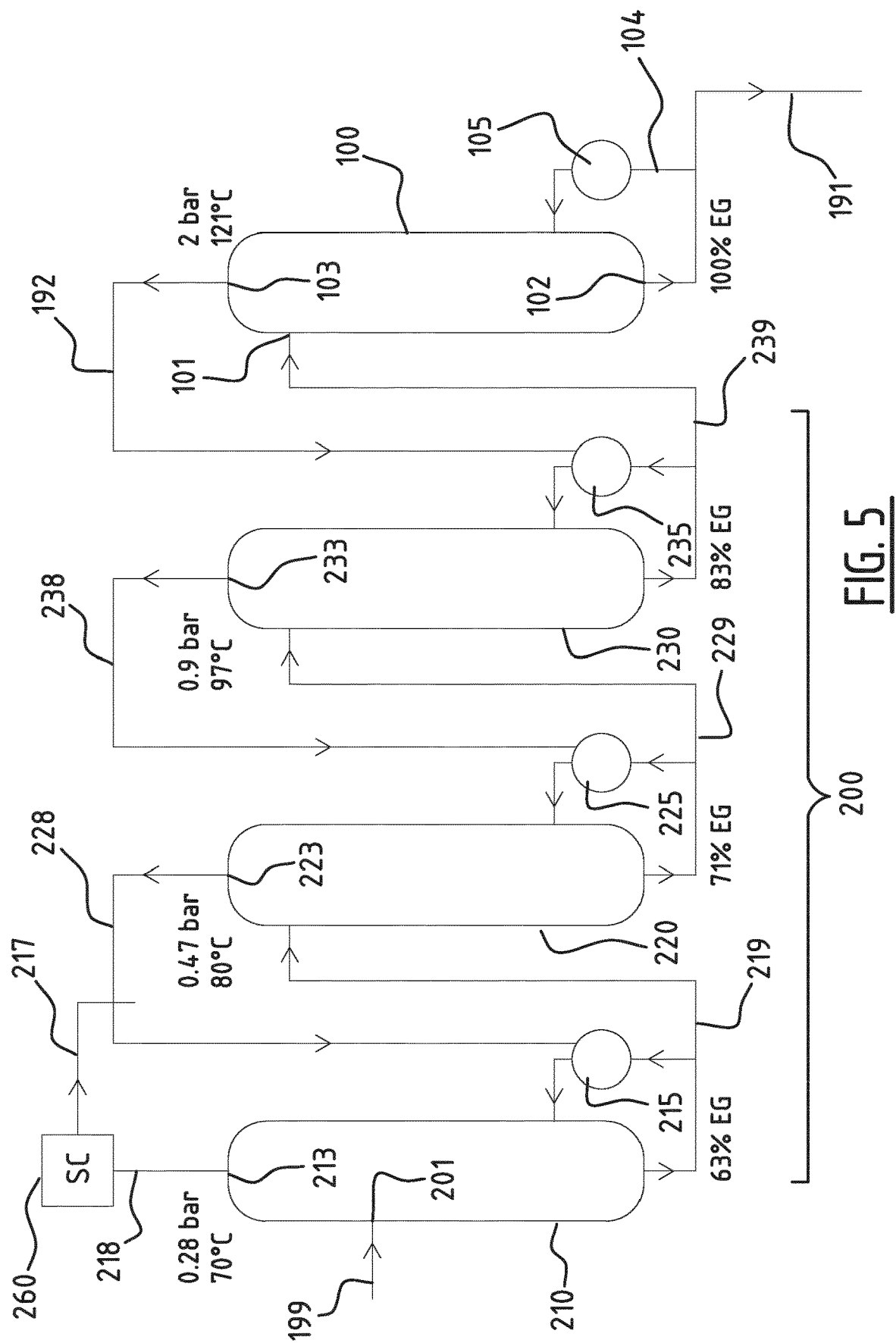
Figure 6:
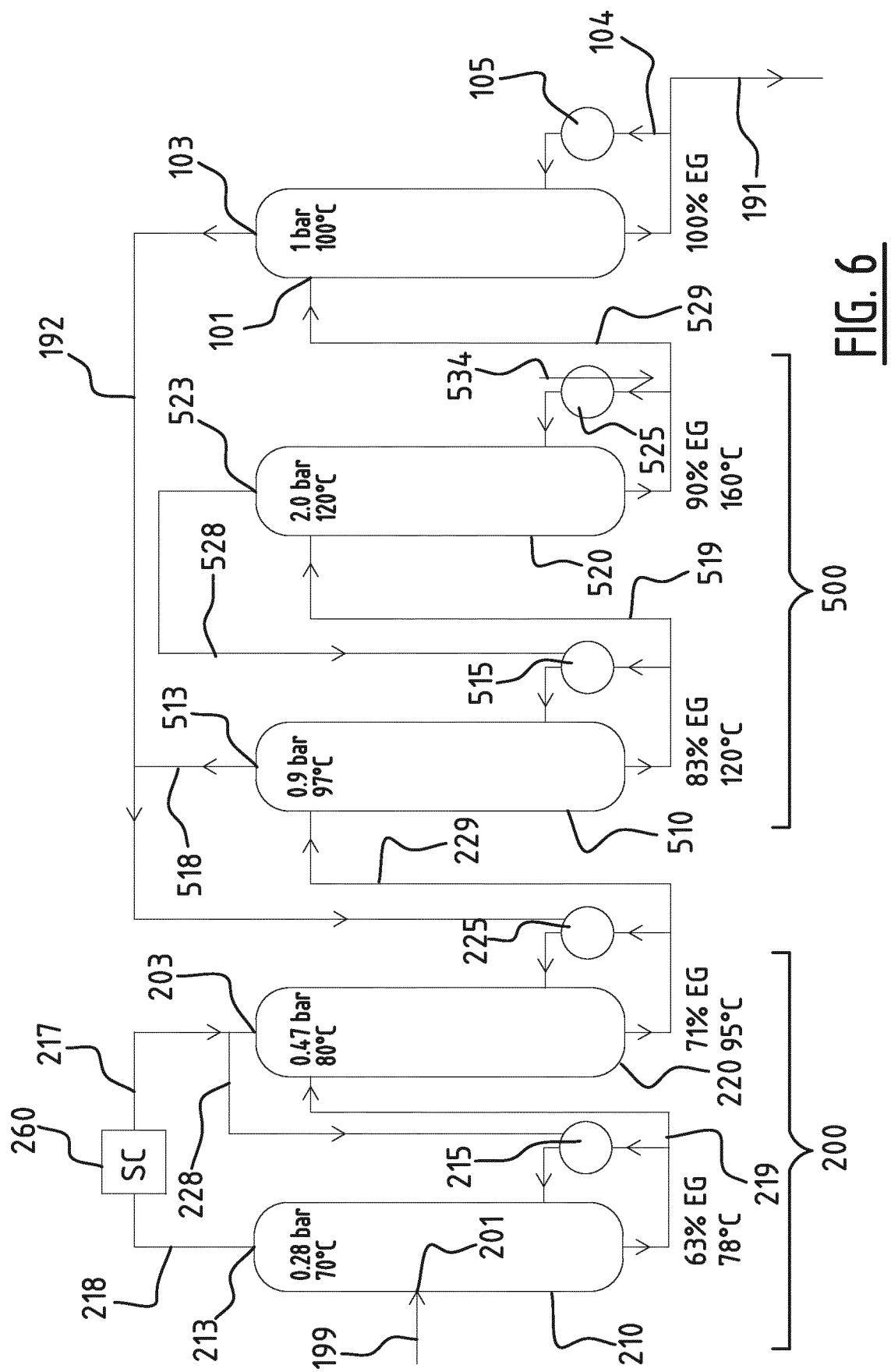
Figure 7:
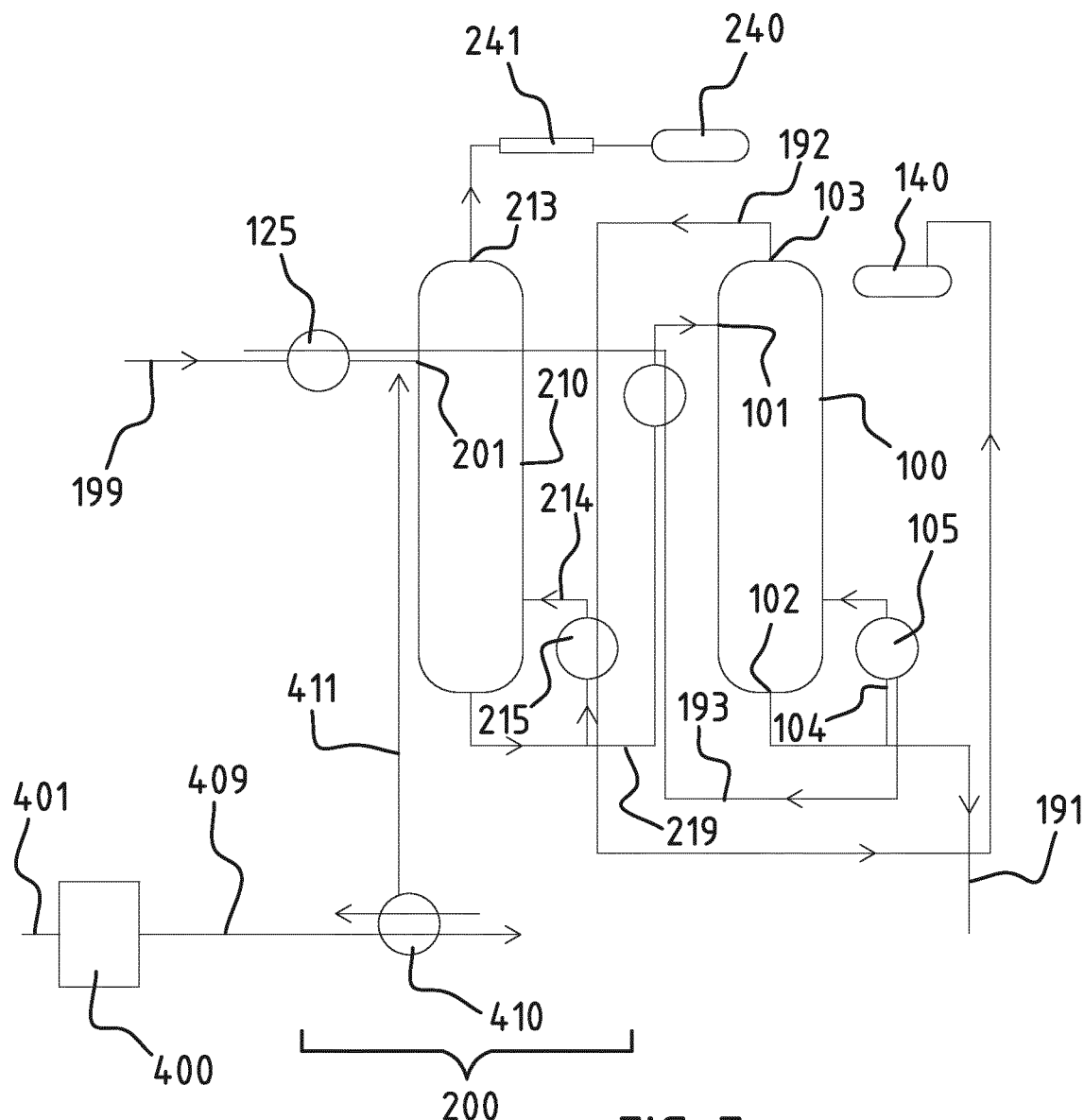
Figure 8:
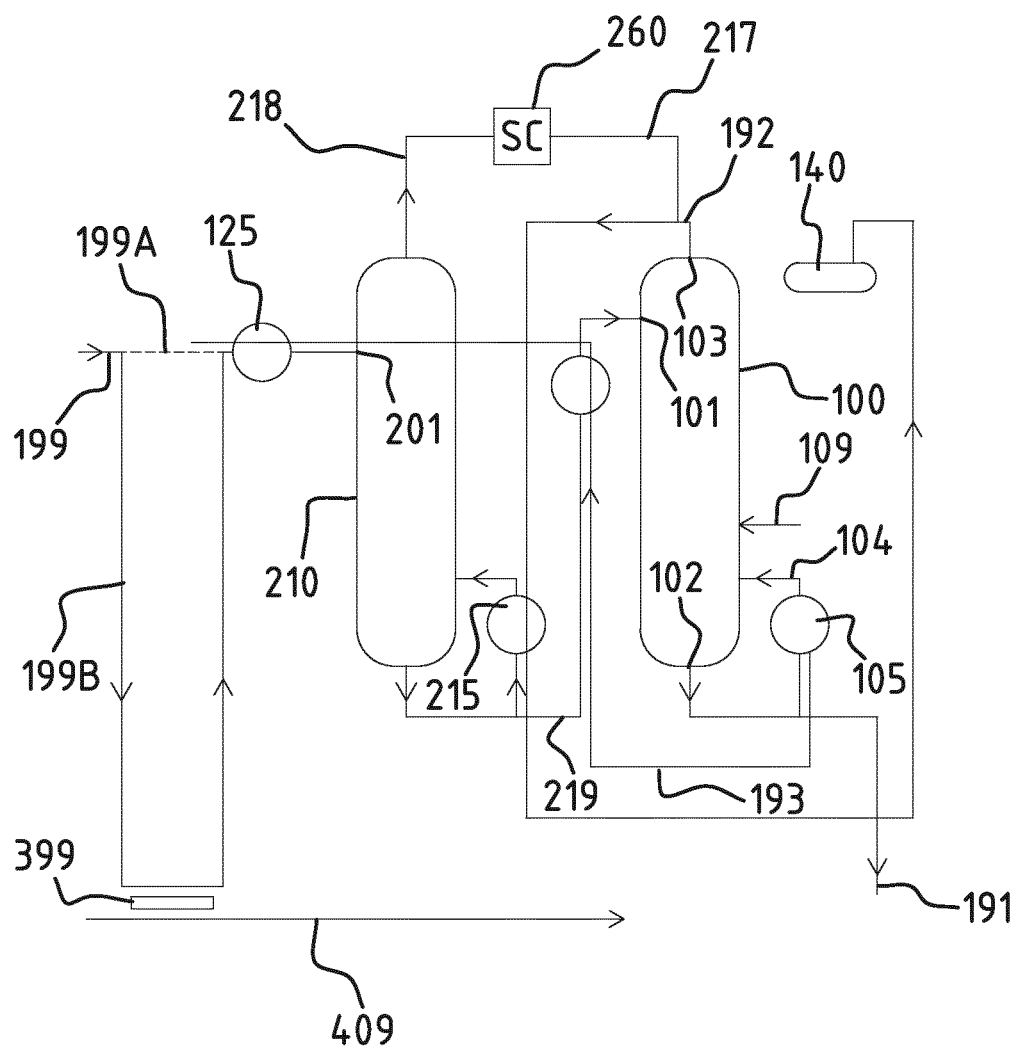
Figure 9:
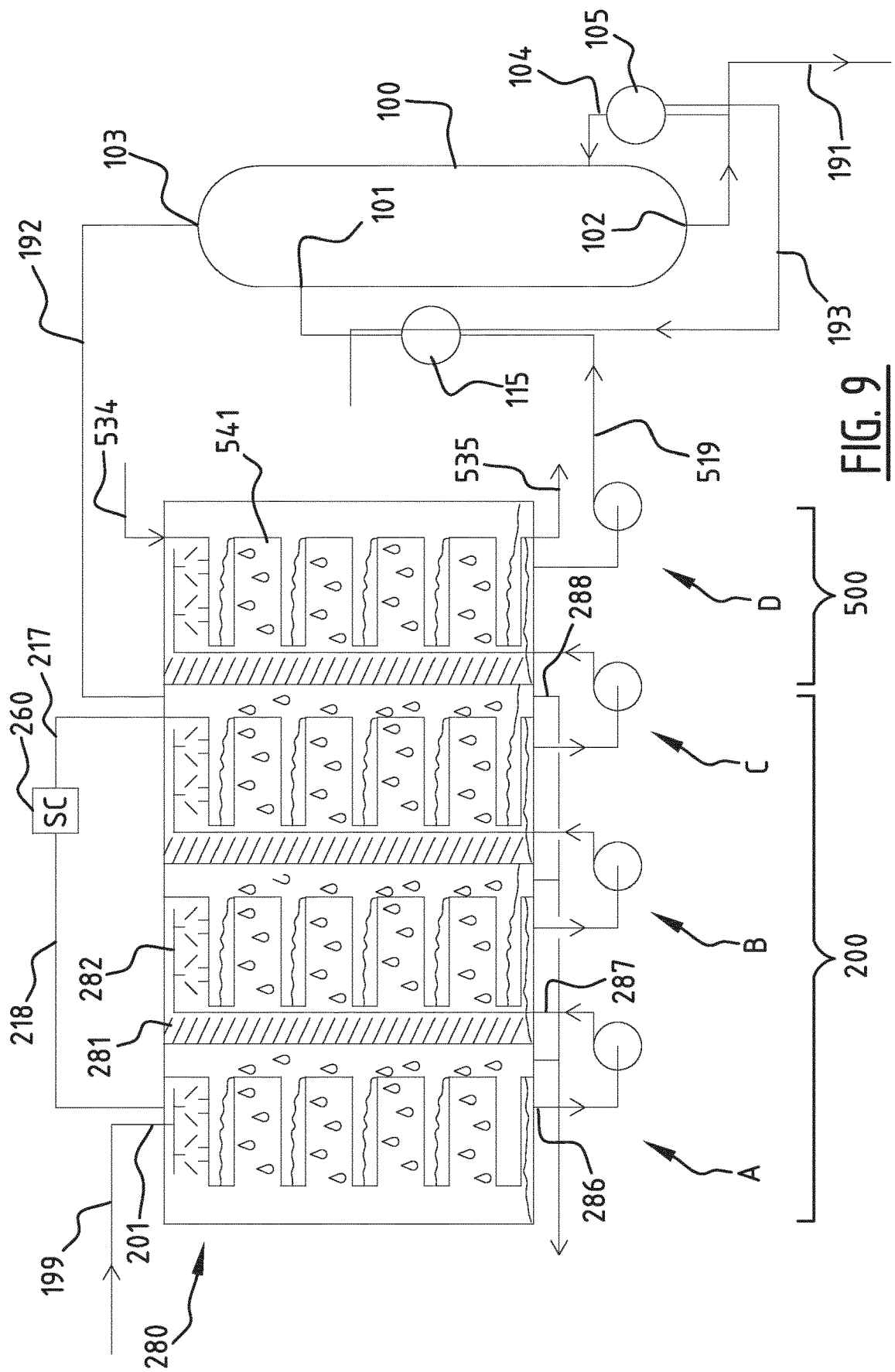
Figure 10:
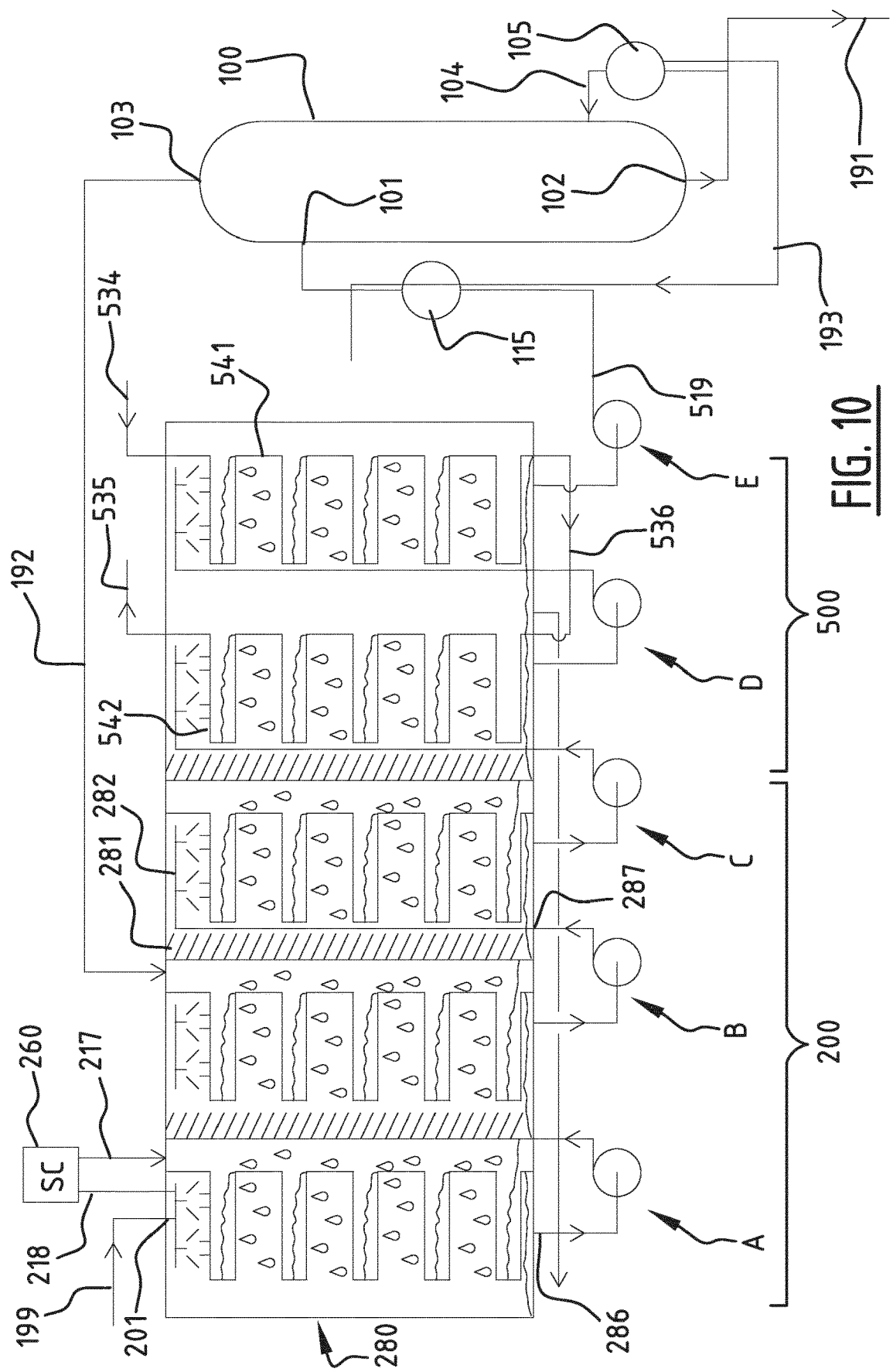
Figure 11:
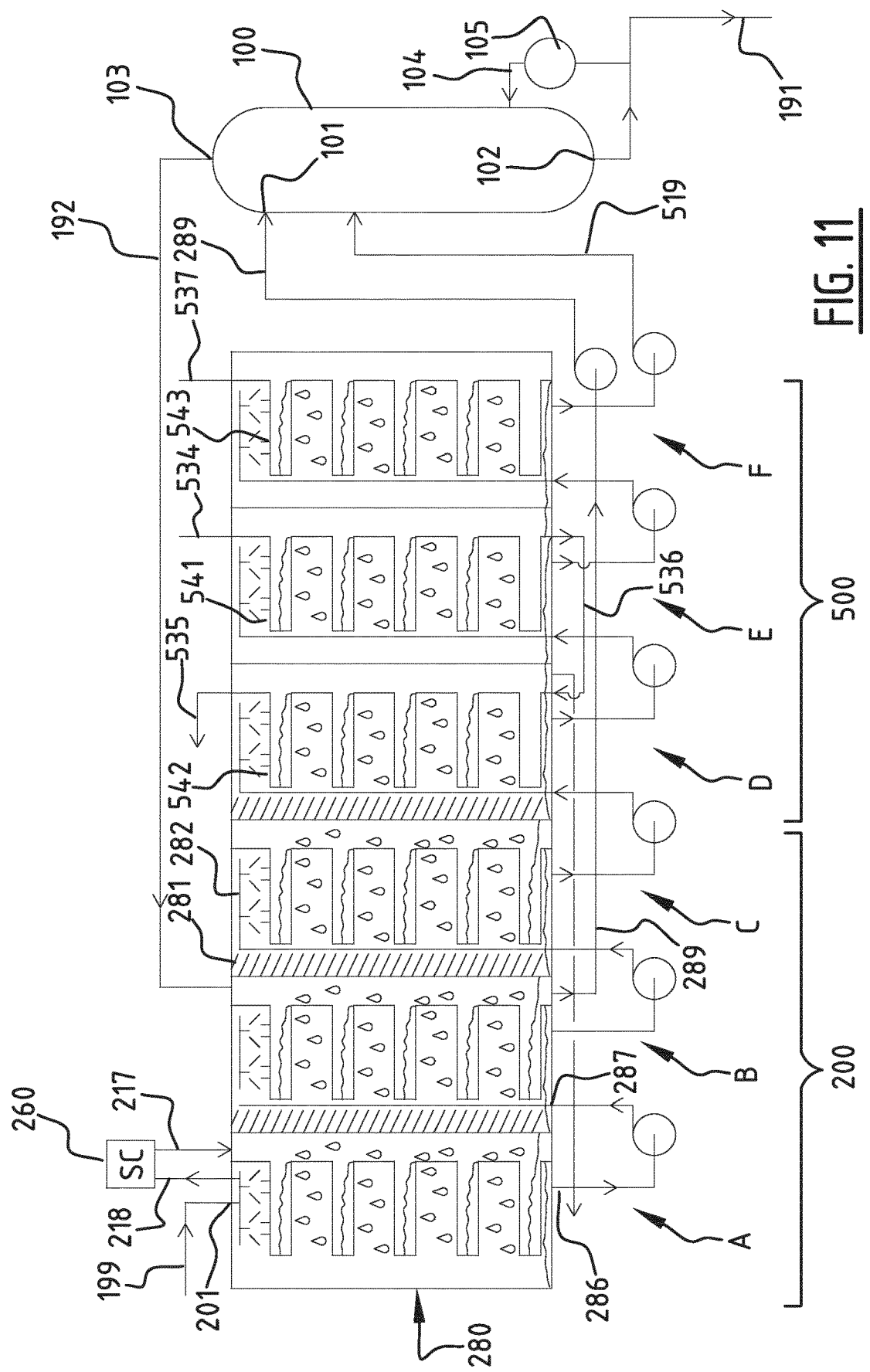

These and other aspects of the invention will be further elucidated with reference to the Figures, wherein:

FIG. 1 schematically shows a first embodiment of the reactor system of the invention, comprising a evaporation stage with a flash vessel and two distillation columns in series:

FIG. 2 schematically shows a second embodiment of the reactor system of the invention, comprising an evaporation stage with a flash vessel:

FIG. 3 schematically shows a third embodiment of the reactor system of the invention, comprising an evaporation stage embodied as a multi-effect distillation installation:

FIGS. 4, 5 and 6 schematically show variations of the first embodiment, wherein use is made of a steam compressor:

FIGS. 7 and 8 schematically show variations of the second embodiment:

FIG. 9-11 schematically show variations of the third embodiment.

DETAILED DISCUSSION OF ILLUSTRATED EMBODIMENTS

The figures are not drawn to scale. The same reference numerals in different figures refer to equal or corresponding elements. Where reference is made to bars, this refers to the absolute pressure. Thus 1 bar is $10^5$ Pa. Each figure shows the reactor system of the invention comprising a distillation stage 100 and an evaporation stage 200. The distillation stage is in the embodiments of FIG. 1-10 embodied as a distillation column. In the embodiment of FIG. 11, the distillation stage is an effect in a multi-effect distillation installation. The distillation stage 100 may be corresponding to a distillation column 220, 230 or effect in the evaporation stage 200, but that is not necessary. In any case, the distillation stage 100 is driven by power from outside the reactor system, such as high-pressure steam (not shown in the figures).

It is observed for clarity that the reactor system of the invention is suitably preceded by further reactor systems in which the mixture of polyalcohol compound, preferably glycol, for instance ethylene glycol, and water is generated. Typically, said mixture contains any further compound, which is removed from the mixture in one or more pre-treatments. For instance, a glycol such as ethylene glycol, is used for the catalysed depolymerisation of a polyester or polyamide or the like. One specific example is the catalysed depolymerisation of polyethylene terephthalate in ethylene glycol, wherein water is added for cooling and separation purposes, so as to remove catalyst and oligomers by means of a centrifuge treatment. The resulting mixture will comprise particulate contaminations to be filtered out and monomer for the polyester, such as BHET (bis-hydroxyethyl terephthalate), which is to be separated via crystallisation and a solid-liquid separation.

As will be elaborated hereinafter, the catalysed depolymerisation may be carried out in a batch-mode and at a temperature close to the boiling point of the glycol (typically ethylene glycol), thus for instance in the range of 160-200° C., preferably at 180-200° C. The emptying of the depolymerisation reactor leads to liberation of heat. In specific implementations of the process and the reactor system of the invention, this heat is reused in the dehydration of the glycol.

Typically, the mixture of the polyalcohol compound and water has a concentration of the polyalcohol compound of at least 40 wt %, preferably at least 45 wt %, more preferably at least 50 wt %. If the concentration of the polyalcohol compound is lower, it can be increased in a suitable manner. This could be carried out by means of a flash vessel, membrane distillation, or any other known technique. It is not critical, as the boiling point of the mixture wherein the polyalcohol compound is lower than 40 wt % is not very sensitive to the concentration.

According to the invention, the purified mixture has a concentration of the polyalcohol compound of at least 90 wt %. The concentration may well be higher, such as at least 95% or at least 99% by weight. In case of the regeneration of a mixture originating from depolymerisation, the mixture will further comprise some dissolved compounds resulting from the depolymerisation, such as monomers, dimers and further oligomers. A concentration of the polyalcohol compound of 100% will then not be feasible. It is not excluded that the regenerated polyalcohol composition comprises some other additives, such as salts.

Turning to FIG. 1, a reactor system is shown with a distillation stage 100, embodied as a distillation column, and an evaporation stage 200, embodied with three substages: a flash vessel 210 and two further columns or vessels 220, 230. A feed stream 199, being a mixture of polyalcohol compound, water and any further additives with an initial concentration of polyalcohol compound, for instance between 40 and 50 wt %, enters the evaporation stage 200 at feed inlet 201. It then enters the first substage 210, which is a flash vessel in the shown embodiment. The flash vessel is boiling under reduced pressure and temperature, in the current embodiment for instance 0.2 bar and 60° C. Steam leaves the flash vessel 210 via steam outlet 213 and is led to a condenser 240 after passing a heat exchanger 241. The stream 219 enriched in the polyalcohol compound leaves the flash vessel at the bottom.

Part thereof 214 returns into the flash vessel 210 after passing a heat exchanger 215. This heat exchanger 215 is also known as a reboiler. Such reboiler may be implemented as being part of the flash vessel 210 (or any distillation column), or be a separate device. A pump may be present as part of the return branch 214, but this is not deemed strictly necessary. The mixture in said return branch 214 is heated in the reboiler/heat exchanger 215 with the steam 228 originating from the second substage 220. As a consequence, the temperature at the bottom of the first substage 210 will be equal or almost equal to that of the steam 228. The term 'almost equal' herein refers to any deviation resulting from heat losses in the transport and in the heat exchange. In one further implementation, distillation trays are present in the flash vessel 210 in between the feed stream 199 and the inlet from the reboiler 215. The distillation trays below the feed stream 199 leads to some distillation without requiring a reflux flow. That turns out to have a positive effect on the effective evaporation, which is beneficial for overall operation. Furthermore, it contributes to operation stability of the flash vessels at relative low pressures, such as pressures below 0.5 bar The operation of the second substage 220 and the third substage 230 is essentially a repetition of that of the first substage 210. However, even if the first substage 210 does not comprise any distillation trays, it is preferred that the second and third substage 220, 230 include such distillation trays. These trays will be located between the feed inlet (from stream 219, 229) and the reboiled stream 224, 234. In comparison to the use of distillation columns for the second and third substage 220, 230 of the evaporation stage, no reflux is present. This is cost effective and allows to operate the substages 220, 230 with top and bottom temperatures that deviate from the effective boiling points. Moreover, and even more importantly, the presence of distillation trays brings the advantage that any polyalcohol, such as ethylene glycol, evaporating with the water in a reboiler, will be washed out from the vapour, and flow back with the feed towards the outlet at the bottom. As a consequence, the water vapour leaving these substages 210, 220, 230 at their steam outlets 213, 223, 233 will contain less contamination with polyalcohol, i.e. have a higher grade of purity.

Furthermore, as will be understood, the pressure, temperature and concentration of polyalcohol compound are higher in the second and the third substage 220, 230 than in the first substage 210. The most downstream substage 230 receives its heat from the steam 192 from the distillation stage 100, which leaves the distillation stage 100 at steam outlet 103. For sake of efficiency, the embodiment illustrated in FIG. 1 but also the embodiments illustrated in other figures are designed so as to reduce the water content of the feed at the inlet 101.

The distillation stage 100 further has an inlet 101 for the enriched stream 239 originating from the evaporation stage 200, a product outlet 102 for the purified stream 191 and a heat exchanger 105 in a return branch 104. Although not indicated in FIG. 1, this heat exchanger 105 is suitably the feed into the distillation stage 100 for high-pressure steam. The remaining, low pressure steam may be led further as stream 193 (see FIG. 2) to transfer remaining heat to the evaporation stage 200. While not shown, the distillation stage 100 furthermore is provided with reflux means as known per se to the skilled person. Herein, the steam 192 leaving the distillation stage 100 at steam outlet 103 is split into a portion towards the reboiler 235 (or alternatively 215 as in FIG. 2) of the preceding stage, and a portion from refluxing. The refluxing involves condensing the steam, leading the condensed steam to a reflux drum and pumping the liquid from the reflux drum back into the top of the distillation stage 100. The exact implementation of the reflux means is open to variations, as the skilled person will understand.

By means of this sequence, wherein the pressure gradually increases, the mixture can be enriched in the polyalcohol compound stepwise, wherein the liberated water is roughly equal in each of the steps (roughly equal implying within a margin of at most 50%, suitably at most 30%). Furthermore, it is achieved herein, that the boiling temperature does not increase too much. As will be visible from Table 1, the steam 228 leaving the distillation stage 100 at steam outlet 103 has a temperature of 100° C. only.

TABLE 1 operation of multistage reactor system shown in FIG. 1.

| stage | | Evaporation stage | | | Distillation |
|---|---|---|---|---|---|
| Substage | Feed | $1^{st}$ substage | $2^{nd}$ substage | $3^{rd}$ substage | stage |
| Glycol (ton/hr) | 5 | 5 | 5 | 5 | 5 |
| Water (ton/hr) | 5 | 3.75 | 2.5 | 1.3 | 0 |
| Glycol concentration (wt %) | 0.5 | 0.57 | 0.67 | 0.8 | 1.0 |
| Evaporated water | | 1.3 | 1.3 | 1.3 | 1.3 |

TABLE 1-continued operation of multistage reactor system shown in FIG. 1.

| stage | | Evaporation stage | | | Distillation |
|---|---|---|---|---|---|
| Substage | Feed | 1st substage | 2nd substage | 3rd substage | stage |
| temperature at top of stage (° C.) | | 60 | 70 | 80 | 100 |
| Pressure at top of stage (bar) | | 0.2 | 0.31 | 0.47 | 1 |
| temperature at bottom of stage (° C.) | | 70 | 80 | 100 | 200 |
| Pressure at bottom of stage (bar) | | 0.22 | 0.33 | 0.49 | 1.1 |
| Required stream pressure (bar) | | 0.31 | 0.49 | 1 | 16 |

FIG. 2 shows schematically the reactor system of the invention according to a second embodiment. In this second embodiment, the evaporation stage 200 comprises a flash vessel 210 only. Such a system benefits less from the stepwise pressure decrease to arrive at a balanced evaporation per stage. However, the operation of the system is feasible and energetically efficient, in the reuse of heat. The principles shown in relation to this figure could also be applied to a reactor system comprising an evaporation stage 200 with a plurality of distillation columns. In the shown system, the high-pressure steam used for heating the distillation stage 100 via heat exchanger 105 to a return branch 104. Thereafter, the stream 193 can still be applied to pre-heat the enriched stream 219 that will enter the distillation stage at its inlet 101. Still, the rest-steam is useful, as it can be used for heating the feed stream 199 that will enter the flash vessel 210 at its feed inlet 201. The increased temperature of the feed 199 will lead to evaporation under the reduced pressure conditions in the evaporation stage 200, such as in the flash vessel 210. This is particularly effective in the method of the invention, wherein the flash vessel operates at a lower pressure than the distillation stage, as the lower pressure results in a lower boiling temperature in the flash vessel 210. Hence, it becomes feasible to evaporate a significant portion of the water in the water-alcohol mixture in the flash vessel, which is clearly beneficial to achieve the desired result of an alcoholic solvent with at most minor parts of water therein.

In the context of the second embodiment, the pressure of the distillation stage is preferably in the range of 1.0-2.0 bar, and the pressure at the flash vessel is suitably 20-60% thereof, for instance at most 1 bar and preferably 0.2-0.6 bar Additionally, as shown in this FIG. 2, the steam 192 produced in the distillation stage 100 is led via heat exchanger 205 to a condenser 140. In this manner, the heat of the distillation stage 100 is effectively transferred to the evaporation stage 200. Furthermore, the distillation stage 100 may be charged via an additional inlet 109 with an additional, predominantly liquid stream. Such additional stream suitably originates from another part of the process, such as a centrifuge. It is typically a hot stream upon entry of the distillation stage 100, so as that its temperature would not disturb operation of the distillation stage 100. It is deemed preferable to add such predominantly liquid stream only in the distillation stage 100, in order to prevent contamination of the preceding stages. While a variety of liquid streams could be used with different degree of purities, it is not excluded that such predominantly liquid stream contains specific contaminations in the form of particles or solutes. One example of a particulate contamination is for instance a heterogeneous catalyst.

FIG. 3 schematically shows the reactor system of the invention according to a third embodiment. Herein, the evaporation stage 200 is embodied as a multi-effect distillation (MED) installation 280. While the first effect 280A of the multi-effect distillation installation may operate at the same low pressure (or even below that pressure) as the first substage 210 of the evaporation stage 200 according to the first embodiment, the volume of the first effect 280A does not need to be as large as that of the flash vessel of the first substage 210 in the first embodiment. In fact, if the capacity of a single first effect 280A would be insufficient, it is feasible to add an extra effect or extra MED installation 280.

The MED installation 280 shown in FIG. 3 comprises three effects 280A, 280B, 280C. Feed 199 enters the evaporation stage 200 and thus the MED installation 280 at feed inlet 201. It then passes a feed distributor 282, which divides the stream into a plurality of droplets, so as to spray the feed onto individual levels of the first effect 280A. Heat is provided into this first stage 280A by means of a heating channel 281. Additionally, the steam 912 from the distillation stage is led to the MED-installation 280. An effect 280A,B,C leads to separation of the water vapor from remaining liquid through a membrane. The water vapour is condensed against a wall. Liberated heat is transmitted through the wall to the adjacent effect. The resulting condensate is removed via a condensate outlet 288. The remaining and concentrated liquid, leaves an effect 280A, 280B, 280C via a second outlet 286, and is thereafter pumped to a corresponding inlet 287 of the subsequent effect, or for the most downstream effect 280C to the distillation stage 100. A pump is needed herein between each stage, so as to achieve that the liquid mixture flows from low pressure to higher pressure. Steam remaining in the most upstream effect 280A is led to a condenser 240.

FIG. 4-6 shows variations of the first embodiment, wherein use is made of a steam compressor 160, 260. The use of a steam compressor 160, 260 is deemed advantageous in the context of the invention, as it allows to limit the effective range between the lowest pressure and the highest pressure in the reactor system when applying the method. Still, the number of substages in the evaporation stage can be sufficiently high or even be optimal.

In the embodiment schematically shown in FIG. 4, a steam condenser 160—also indicated with SC—is arranged between the steam outlet 103 of the distillation stage 100 and a heat exchanger of the evaporation stage 200, and more particularly, the heat exchanger 235 of the substage 230 that is arranged most downstream within the evaporation stage 200, thus at the highest pressure. It would not be impossible to lead to the stream 192 to the heat exchanger of another substage 210, 220. This is particularly feasible if the heat exchanger 235 can be fed with heat from another heat source. Although not indicated in this figure, it is feasible that the steam applied to the heat exchanger 105 of the distillation stage 100 is reused thereafter to heat the enriched stream 239 being fed to the distillation stage 100 and/or to heat (or pre-heat) the mixture of polyalcohol compound and water at another location within the reactor system.

The effect of the steam compressor can be understood from Table 2 and the comparison with Table 1. While the flow rates, and the rate of evaporation of water, are the same in the embodiments without and with steam compressor (FIG. 1 and FIG. 4 respectively), the pressure in the first substage is twice as high in the embodiment with steam compressor than without (0.4-0.44 vs 0.2-0.22 bar). As a consequence, the volume of the $1^{st}$ substage (suitably a flash vessel) can be reduced significantly. Atmospheric pressure is reached in the $3^{rd}$ substage rather than only in the distillation stage. Corresponding thereto, the temperatures are higher in the substages of the evaporation stage, i.e. between 76 and 100° C., rather than between 6° and 80° C. When looking at the required steam pressure, the minimum pressure is 0.64 bar, rather than 0.31 bar. This simplifies handling and construction of the reactor system.

stage 200. The substages are embodied as flash vessel provided with a reboiler 215, 225, 235 and preferably some distillation trays between the feed stream 199 and the inlet from the reboiler 215. The resulting stream of compressed steam 217 is merged with the steam that leaves the steam outlet from a substage that is arranged more downstream. It appears preferred, though not necessary, that said substage is the second substage 220, which is indicated in FIG. 5 and FIG. 6. The resulting stream of steam 228 will be more or less at the outlet pressure of the second substage 220. This steam is then strong enough to maintain the first substage 210 at appropriate pressure and temperature, which are in the example of FIGS. 5 and 6, 0.28 bar and 70° C. for the steam at the steam outlet 103, and 78° C. and 0.3 bar for the enriched liquid mixture 219.

In the embodiment of FIG. 5, the distillation stage is operated at a pressure of 2 bar. It will be understood by the skilled person, that one may alternatively operate this distillation stage at a lower pressure, up to 1 bar, and then apply another steam compressor to the steam 192, as shown in FIG. 4.

In the embodiment of FIG. 6, a concentration stage 500 is present upstream of the distillation stage 100 and downstream of the evaporation stage 200. This concentration stage is heated by means of a stream of heat 534, typically steam, originating from an external heat source, more particularly waste heat, such as waste heat from an emptied

TABLE 2 settings for the operation of the reactor system shown in FIG. 4

| stage | | Evaporation stage | | | Distillation |
|---|---|---|---|---|---|
| Substage | Feed | $1^{st}$ substage | $2^{nd}$ substage | $3^{rd}$ substage | stage |
| Glycol (ton/hr) | 5 | 5 | 5 | 5 | 5 |
| Water (ton/hr) | 5 | 3.75 | 2.5 | 1.3 | 0 |
| Glycol concentration (wt %) | 0.5 | 0.57 | 0.67 | 0.8 | 1.0 |
| Evaporated water (ton/hr) | | 1.3 | 1.3 | 1.3 | 1.3 |
| temperature at top of stage (° C.) | | 76 | 87 | 100 | 100 |
| Pressure at top of stage (bar) | | 0.4 | 0.64 | 1 | 1 |
| temperature at bottom of stage (° C.) | | 87 | 100 | 121 | 200 |
| Pressure at bottom of stage (bar) | | 0.44 | 0.64 | 1.1 | 1.1 |
| Required stream pressure (bar) | | 0.64 | 1 | 2 | 16 |

It is observed that the present example uses steam compression from 1 to 2 bar, which is known to provide sufficient power so that the temperature in the $3^{rd}$ substage can be 100° C. at 1 bar. It is clearly not excluded that the steam compressor would compress the steam less strongly, for instance to increase the pressure with 50% (or 0.5 bar), rather than 100% (1 bar) relative to the pressure in the distillation stage. Less pressure increase facilitates a simpler steam compressor, with the effect that the pressure in the first substage will be reduced in corresponding manner. Evidently, one could additionally choose to increase the pressure in the distillation stage 100 and reduce the steam compression ratio (=output pressure versus input pressure) relative to the ratio of 2 indicated in Table 2.

In the embodiments shown in FIG. 5 and FIG. 6, a steam compressor 260 is arranged in the steam outlet 218 at the steam outlet 213 of the first substage 210 of the evaporation reactor. Therefore, the steam 192 from the distillation stage 100 is led directly to the most downstream vessel 220 in the evaporation stage 200, passing over the concentration stage 500.

The concentration stage 500 comprises in this embodiment two substages 510, 520, each of which is embodied, in the illustrated embodiment, corresponding to the substages 210, 220 of the evaporation stage 200. Hence the vessels 510, 520 are each provided with feed inlet, steam outlet 513, 523, reboilers 515, 525. The mixture flows from the second substage 220 as a stream 229 enriched in polyalcohol to the inlet of the third substage 510. The further enriched mixture 519 flows or is flown (by means of a pump, if needed) to the fourth substage 520. The again further enriched mixture 529 flows to the inlet 101 of the distillation stage 100. In the illustrated embodiment, the heat stream 534 has a temperature of more than 190° C. and its volume is set so as to allow to heat the fourth substage 520 to achieve a temperature of 120° C. at 2 bar pressure at its steam outlet 523. In the third substage 510, the temperature at the steam outlet 513 is 97° C. at a pressure of 0.9 bar. The temperature of the mixture 519 is about 120° C. and that of the mixture 529 even 160° C. In view of the chosen pressures, there is no need to apply steam compression to the steam 192 originating from the distillation stage 100.

Rather than choosing that the evaporation rate is equal in all substages 210, 220 of the evaporation stage 200, 510, 520 of the concentration stage and in the distillation stage 100, it is feasible and may well be useful, to set the evaporation rates in a manner which would minimize overall reactor sizes. For instance, one may choose to reduce the evaporation rate in the first substage 210, while another substage could be increased. For instance, the second substage 220 could be larger and/or could be embodied as two vessels in parallel.

FIG. 7-8 shows variants of the second embodiment of the invention as schematically shown in FIG. 2. FIG. 7 shows an option to enable further reuse of heat. This is done by means of heat exchange on a stream 409. Additionally, a predominantly liquid stream may be added into the distillation stage 100. The stream 409 and the additional inlet liquid stream 109 originate for instance from a reactor, such as a depolymerisation reactor which operates at a temperature higher than the temperatures used in the operation of the method of the present invention. The stream 409 originates from a buffer tank 400, designed to as to convert temporal batches 401 originating from a batch reactor into a continuous stream 409. Heat exchanging occurs in heat exchanger 410. The receiving stream 411 is for instance water and/or steam, but could be any type of heat transfer medium, including oil. The receiving stream 411 can thereafter be heat exchanged with the feed 199, but is alternatively applied to heat the flash vessel 210 directly, for instance as a jacket around the flash vessel 210.

In the embodiment shown in FIG. 8, steam compression is applied to the steam output 218 of the first (and only) substage 210 of the evaporation stage 200. This occurs by means of steam compressor 260. The stream of compressed steam 217 is merged with a stream of steam originating from a downstream stage, in this example the steam 192 originating from the distillation stage 100. It is furthermore shown in this FIG. 8, that the stream 409 (originating from a reactor) is heat-exchanged in heat exchanger 399 with the feed 199. In order to match the available heat in stream 409 with the heat needed for the feed 199, the feed is herein split into a first feedline 199A, which does not pass the heat exchanger 399 and a second feedline 199B, which passes the heat exchanger 399. The first feedline 199A thus constitutes a bypass. By controlling the flow rates in the first and the second feedline 199A, 199B, the feed heating can be tuned so as to be efficient without obtaining a too vigorous boiling in the flash vessel 210. Instead of a heat exchanger 399, a kettle boiler may be used. Such kettle boiler will operate under the vacuum of the distillation stage 100. It is not excluded that some glycol, such as ethylene glycol is added, so as to ensure that the viscosity of the enriched mixture remains correct.

FIG. 9-11 show three variants on the third embodiment using a multi-effect distillation (MED) installation 280. In the embodiment schematically shown in FIG. 9, the MED-installation 280 comprises four effects 280A-280D. In the embodiment of FIG. 10, the MED-installation 280 comprises five effects 280A-280E. In the embodiment of FIG. 11, the MED-installation 280 comprises six effects 280A-280F. Notwithstanding the integration into a single MED-installation 280, there is a conceptual distinction between the first three stages 280A-C and the remaining stages 280D, 280E, 280F. The first three stages 280A-C constitute the evaporation stage as has been discussed hereinabove. This evaporation stage 200 is heated by means of the steam 192 originating from the distillation stage 100. As in the implementation with separate vessels and columns 210, 220, 230, each effect operated at a separate pressure, wherein the pressure increases from the first effect 280A towards the third effect 280C.

The remaining effects 280D, 280E, 280F are part of a concentration stage 500. No use is made of steam evaporation herein. Rather, the effects are embodied as heat exchangers, wherein another liquid or gas flows through channels or tubes and does not get into contact with the feed stream of the said effects. The liquid or gas typically originates from an external heat source. That may be a stream from a reactor, or alternatively based on waste heat. More particularly a heat stream 534 is supplied and is circulated via tubes 541 through the effect 280D (in FIG. 9) of the effects 280D and 280E (FIGS. 10 and 11). It leaves the stage as stream 535, and is then discarded as waste (although it is not excluded that the stream 535 would be reused). The tubes can be embodied according to any suitable shape, include trays with holes. The resulting mixture concentrated 519 is led to the inlet of the distillation stage 100

In the FIGS. 10 and 11, the heat stream 534 is led from the fifth effect 280E to the fourth effect 280D via extension 536. It is observed that merely heat exchange occurs in these effects 280D, 280E. As a consequence, the pressure is equal in both effects 280D, 280E and a separation barrier 281 is not needed between the two effects 280D, 280E.

In the FIG. 11, the concentration stage 500 comprises a sixth effect 280F, which is fed by a heat stream 537, extending through the effect by means of a circulation system 543. This sixth effect 280F is held at the same pressure as the preceding effects 280D, 280E of the concentration stage 500. In the embodiment shown in FIG. 11, a further recycle 289 of steam is provided. This is recycle from the second substage or effect 280B back to the distillation stage 100. Hence, steam 192 is provided from the distillation stage 100 to the top of the second effect 280B, and is after passing this second effect 280B returned to the distillation stage 100 via recycle 289. As will be understood, the recycle may be either steam or liquid or a mixture of both.

Although not shown, it is not excluded that part of the steam 192 originating from the distillation stage 100 is led to the first effect 280A, or that the steam/liquid from the second effect 280B is further led to the first effect 280A. Typically, in multi-effect distillation, heat will be transmitted via the separation wall or barrier 281 between the effects. Although merely shown diagrammatically in the FIGS. 9-11, each effect is preferably designed in corresponding manner so as to allow integration. The construction of a multi-effect distillation installation is known per se and feasible for an expert on multi-effect distillation installations.

In one example of operating the installation shown in FIG. 9. the enriched stream leaving the first effect 280A at the outlet 286 towards the inlet 287 of the second effect 280B, has a temperature of 70° C. (with about 57 wt % glycol). At the bottom of the second effect 280B, the temperature is 80° C. (with about 67% glycol). At the bottom of the third effect, the temperature becomes 100° C. (with about 80% glycol). The fourth effect 280D, that is heated with a separate heat stream 419, for instance entering the fourth effect at a temperature of 195-200° C. results in a temperature of 135° C. for the enriched mixture 219 and a glycol concentration with would arrive at 90 wt %.

FIG. 9 shows additionally the use of a steam compressor 260, which compresses steam from the first effect 280A to a higher pressure, herein about 1 bar, rather than (or optionally in addition to) transferring said steam to a condenser. The increased flow of steam into the third effect 280C is effective to boost the evaporation. As a consequence, it becomes feasible to reduce the size of the distillation column in the distillation stage 100. It is observed for sake of clarity that the steam 192 originating from the distillation stage 100 as well as the stream of compressed steam 217 would enter into the heating channel 281 of the MED-installation 280.

This application is based on Netherland Patent Application Serial No. 2022037 filed with Netherland Patent Office on Nov. 21, 2018, the entire contents of which are hereby incorporated herein by reference.

LIST OF REFERENCE NUMERALS 100 distillation stage
101 inlet for a stream (239, 219) enriched in the polyalcohol compound and arriving from the evaporation stage 200
102 outlet for the purified product stream 191
103 outlet for a steam output 192
104 return branch
105 heat exchanger
109 inlet for predominantly liquid rest stream
125 heat exchanger in the feed stream
140 condenser
160 steam compressor
191 purified product stream
192 steam output stream
193 heat stream (for instance steam) from the distillation stage 100 to the evaporation stage 200
199 feed stream
199A feed stream shortcut
199B feed stream passing heat exchanger 420 with hot outlet stream
200 evaporation stage
201 feed inlet
210 first substage of evaporation stage 200 (for instance embodied as flash vessel)
213 steam outlet of the first substage 210
214 return branch (from enriched stream 219)
215 heat exchanger
218 steam outlet stream
217 stream of compressed steam
219 mixture stream enriched in polyalcohol compound
220 second substage of evaporation stage 200 (for instance embodied as distillation column)
223 steam outlet of the substage 220
224 return branch (from enriched stream 229)
225 heat exchanger
228 stem output stream being led to heat exchanger 215, 315 of preceding substage 210, 310
229 mixture stream enriched in polyalcohol compound
230 third substage of evaporation stage 200 (for instance embodied as distillation column)
233 steam outlet of the substage 230
234 return branch (from enriched stream 239)
235 heat exchanger
238 stem output stream being led to heat exchanger 225 of preceding substage 220
239 mixture stream enriched in polyalcohol compound
240 condenser (coupled to the first substage 210 when embodied as flash vessel)
241 heat exchanger
260 steam compressor
280 multi-effect distillation installation
280A,B,C,D,E,F individual effects of the multi-effect distillation installation 280
281 heating channels between individual effects 280A, B,C
282 feed distributor
286 outlet for stream enriched in the polyalcohol compound
287 inlet for stream enriched in the polyalcohol compound
288 outlet for condensate
289 channel leading stream enriched in the polyalcohol compound from the effect inlet 287 to the distributor 282
310 further substage of evaporation stage 200
314 return branch (from enriched stream 319)
315 heat exchanger
318 stem output stream being led to heat exchanger 215 of preceding substage 210
319 mixture stream enriched in polyalcohol compound
399 heat exchanger between hot outlet stream 409 and feed stream 199B
400 buffer tank
401 inlet for buffer tank
409 hot outlet stream
410 heat exchanger for outlet stream
411 heat stream between heat exchanger 410 and substage (210) of evaporation stage
416 outlet for heat stream after heating multieffect distillation installation 280
417 connection for heat stream between effects D, E in multi-effect distillation installation 280
418, 419, 420 heat stream for heating effects D, E, F of multieffect distillation installation 280
434 waste heat stream

The invention claimed is:

1. A method of at least partially separating a polyalcohol compound from water, so as to obtain a purified product stream comprising the polyalcohol compound in an output concentration of at least 90 wt %, wherein the method comprises steps of:
providing a mixture of the polyalcohol compound and water, said mixture having a polyalcohol concentration;
feeding the mixture to an inlet of an evaporation stage and increasing the polyalcohol concentration of the mixture in the evaporation stage, wherein at least a portion of the evaporation stage is operated at a first pressure;
treating the mixture in a distillation stage provided with a reflux means operating at a pressure up to 1.5 atmospheres to obtain the purified product stream comprising the polyalcohol compound in the output concentration of at least 90 wt %,
wherein the distillation stage is operated at a second pressure,
wherein the distillation stage is operated to produce a steam output,
wherein the steam output is optionally compressed to a third pressure and is supplied to the evaporation stage,
wherein at least one of the second pressure and the third pressure is higher than the first pressure, and
wherein the evaporation stage comprises at least one flash vessel and the at least one flash vessel is provided with a reboiler that generates steam and provides the steam at a bottom side of the at least one flash vessel and the at least one flash vessel does not contain any means for refluxing.

2. The method as claimed in claim 1, wherein the evaporation stage is operated such that an evaporation temperature within the evaporation stage is at most 30° C. above a boiling point of pure water at atmospheric pressure.

3. The method as claimed in claim 1, wherein the at least one flash vessel comprises distillation trays between a feed inlet and an inlet from a recycle stream from the reboiler.

4. The method as claimed in claim 1, wherein the evaporation stage comprises a plurality of vessels in series, each vessel working at a different pressure.

5. The method as claimed in claim 4, wherein the steam output of the distillation stage is coupled to a most downstream vessel of the evaporation stage.

6. The method as claimed in claim 4, wherein a most downstream vessel of the evaporation stage has a steam output that is coupled to a directly preceding vessel by means of heat-exchanging, and wherein the most downstream vessel is operated at a higher pressure than the directly preceding vessel.

7. The method as claimed in claim 6, wherein the steam output of the distillation stage is compressed to the third pressure by means of a steam compressor.

8. The method as claimed in claim 1, wherein the evaporation stage comprises a multiple-effect evaporator.

9. The method as claimed in claim 1, wherein the polyalcohol concentration of the mixture of the polyalcohol compound and the water is at least 40 wt %.

10. The method as claimed in claim 1, wherein the polyalcohol compound is a glycol compound.

11. The method as claimed in claim 1, wherein the mixture of the polyalcohol compound and water further comprises oligomers resulting from depolymerisation of a condensation polymer.

12. The method as claimed in claim 1, wherein the mixture is treated in a concentration stage after passing the evaporation stage, to further increase the polyalcohol concentration, wherein the mixture is heated in said concentration stage by means of waste heat supplied from a reactor.

13. The method of claim 1, wherein the reflux means operates at a pressure at or below atmospheric pressure.

* * * * *